United States Patent [19] [11] 4,092,110
Adolphi et al. [45] May 30, 1978

[54] METHOD OF PROTECTING WOOD WITH PERFLUOROALKANE SULFONATES

[75] Inventors: Heinrich Adolphi; Matthias Schwarzmann, both of Limburgerhof; Peter Heinze, Ellerstadt, all of Germany

[73] Assignee: BASF Aktiengesellschaft, Ludwigshafen, Germany

[21] Appl. No.: 770,094

[22] Filed: Feb. 18, 1977

[30] Foreign Application Priority Data

Mar. 6, 1976 Germany .................................. 2609311

[51] Int. Cl.² .......................... A01N 9/12; A01N 9/24; B27K 3/36
[52] U.S. Cl. .......................................... 21/7; 424/315; 424/DIG. 11; 427/440
[58] Field of Search ........ 21/7, 58; 424/315, DIG. 11; 427/440; 52/168, 517

[56] References Cited

U.S. PATENT DOCUMENTS

| 2,732,398 | 1/1956 | Brice et al. | 252/71 |
| 2,840,501 | 6/1958 | Mevli | 424/315 |
| 3,488,425 | 1/1970 | Gilbert et al. | 424/315 |
| 3,639,474 | 2/1972 | Harrington et al. | 424/315 |

FOREIGN PATENT DOCUMENTS

| 2,234,837 | 1/1974 | Germany. | |
| 454,759 | 2/1950 | Italy | 424/315 |

Primary Examiner—Morris O. Wolk
Assistant Examiner—Bradley Garris
Attorney, Agent, or Firm—Keil, Thompson & Shurtleff

[57] ABSTRACT

Wood preservatives for protecting wood or wood-base materials against animal pests, and which contain a perfluoroalkane sulfonate of the formula $C_nF_{2n+1}$—$SO_3M$ where $n$ is one of the integers from 1–14 and M denotes hydrogen or a cation, and a process for protecting wood or wood-base materials against animal pests with these compounds.

6 Claims, No Drawings

METHOD OF PROTECTING WOOD WITH PERFLUOROALKANE SULFONATES

The present invention relates to wood preservatives for protecting wood or wood-base materials against animal pests, and which contain a perfluoroalkane sulfonate, and a process for protecting wood or wood-base materials against animal pests with these compounds.

Particular importance attaches to the protection of wood and wood-base materials against animal pests. Especially in the tropics and subtropics, considerable damage is caused by insects. The most dangerous wood destroyers are termites (Reticulitermes).

It is known (German Printed Application DAS 1,138,277) to combat insects with the active ingredient α-naphthyl N-methylcarbamate.

We have now found that compounds of the formula $$C_nF_{2n+1}-SO_3M,$$

where $n$ is one of the integers from 1 to 14 and M denotes hydrogen or a cation, have a strong action on wood-destroying insects, especially termites. It is preferred to use perfluoroalkane sulfonates having the above formula and in which $n$ denotes one of the integers from 3 to 10, especially 4 to 8. The alkyl radical may be linear or branched. Examples of cations are an ion of an alkali metal (sodium, potassium) or of an equivalent of an alkaline earth metal (magnesium, calcium), an ammonium ion, and an ion of a substituted amine ($N(CH_3)_3H^+$, $N(C_2H_5)_4^+$, $N(CH_3)_2H_2^+$, $N(C_4H_9)_4^+$).

The preparation of the active ingredients is described in German Laid-Open Application DOS 2,234,837: perfluoroalkanesulfonic acid fluorides of the formula $$CF_3-[CF_{2n}]-SO_2F,$$

where $n$ denotes one of the integers from 1 to 14, are prepared by electrolysis of a mixture of alkanesulfonic acid fluorides of the formula $$CH_3-[CH_{2n}]-SO_2F,$$

where $n$ has the above meaning, and hydrogen fluoride. Electrolysis is carried out at 4 to 7.5 volts and alkanesulfonic acid fluoride concentrations, based on HF, of from 0.3 to 5 wt%.

The perfluoroalkanesulfonic acid fluorides are hydrolyzed to the free acids and converted to the corresponding salts with basic compounds, e.g., NaOH, KOH, Ca(OH)$_2$.

Examples of starting compounds for the electrolysis are n-propane-, 2,2-dimethylpropane-, isobutane-, n-butane-, 1-methylbutane-, 2,2-dimethylbutane-, 2,3-dimethylbutane-, 2-methylhexane-, 3-methylhexane-, 3-ethylpentane-, 2,2,3-trimethylbutane-, 2,4-dimethylpentane-, 2,3-dimethylpentane-, 3,3-dimethylpentane-, 2,2-dimethylpentane-, 2-methylheptane-, 4-methylheptane-, 3-methylheptane-, 2,2,3-trimethylpentane-, 2,2,4-trimethylpentane-, 2,3,3-trimethylpentane-, 2,3,4-trimethylpentane-, 2,2,3,3-tetramethylbutane-, 2-methylpentane-, 3-methylpentane-, n-decane-, n-undecane-, n-dodecane-, n-tridecane-, n-tetradecane-, and especially n-pentane-, n-hexane-, n-heptane-, n-octane- and n-nonane-1-sulfonic acid fluoride.

The corresponding perfluoroalkane sulfonates and sulfonic acids are the active ingredients to be used according to the invention. Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient. The wood may be treated for instance by impregnation, dipping, painting or spraying with a solution of the active ingredient. The active ingredient may also be admixed to the glue to be used in the manufacture of wood-base materials, or to the coating agents, e.g., oil and emulsion paints, to be used for coating the wood. The wood may be impregnated for instance in a cylinder under a vacuum or at superatmospheric pressure.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possible solvent or oil.

Examples or surfactants are: alkali metal, alkaline earth metal and ammonium salts of ligninsulfonic acid, naphthalenesulfonic acid, phenolsulfonic acids, alkalaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of napthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

The formulations contain from 0.1 to 95, preferably from 0.5 to 90, wt% of active ingredient.

There may be added to the compositions or individual active ingredients oils of various types, fungicides, insecticides or bactericides.

The amount used of the agents according to the invention varies and depends in essence on the type of effect desired; it is usually from 1 to 10, preferably 2 to 8, g of active ingredient per m² of wood surface.

The following examples demonstrate the biological action. The following active ingredients were employed:
1. potassium perfluorooctane sulfonate
    $C_8F_{17}SO_3K$
2. sodium perfluorooctane sulfonate
    $C_8F_{17}SO_3Na$
3. sodium perfluorobutane sulfonate
    $C_4F_9SO_3Na$ Comparative agent, disclosed in German Printed Application DAS 1,138,277

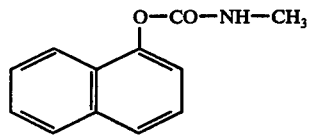

EXAMPLE 1

Pine beams 4×6×70cm, the ends of which have been sealed with a plastics mass, are coated with 2 wt% solutions of the active ingredients in isopropanol. 200 ml of solution is used per m² of surface area, this rate being equivalent to 4 g of active ingredient per m². 8 days after treatment, blocks 4 cm in length are cut from the beams and the ends sealed. These blocks are then subjected to termite attack (Reticulitermes lucifugus). The blocks are embedded in moist expanded clay and about 200 termites are placed thereon. The kill rate and the amount of wood eaten away by the termites are assessed after 4 to 8 weeks.

To be able to assess the penetration of the active ingredient, 2, 4 and 8 mm are planed off all sides of sample blocks 8 days after treatment and tested in the same manner.
Results:

| Compound | | % Mortality after 4 weeks | after 8 weeks |
| --- | --- | --- | --- |
| No. 2 | original surface | 100 | 100 |
| | 2 mm planed off | 100 | 100 |
| | 4 mm planed off | 80 | 100 |
| | 6 mm planed off | 60 | 100 |
| | 8 mm planed off | 60 | 80 |
| No. 3 | original surface | 100 | 100 |
| | 2 mm planed off | 100 | 100 |
| | 4 mm planed off | 100 | 100 |
| | 6 mm planed off | 90 | 100 |
| | 8 mm planed off | 50 | 80 |
| Comparative agent | original surface | 100 | 100 |
| | 2 mm planed off | 100 | 100 |
| | 4 mm planed off | 60 | 100 |
| | 6 mm planed off | ineffective | ineffective |

EXAMPLE 2

(Weathering test in accordance with DIN 52,172, p. 3)

Pine beams 1.5×2.5×50cm in size are used. The active ingredients are applied as described in Example 1. The amount of active ingredient applied is equivalent to 4 g/m². 8 days after treatment blocks 5 cm in length are cut from the beams and stored on one of the narrow sides in a ventilated drying cabinet for 4 and 8 weeks at 40° C. The biological action was determined with the aid of termites (Reticulitermes lucifugus) in the same manner as in Example 1.
Results:

| Compound | Storage period | % Mortality after 4 weeks | after 8 weeks |
| --- | --- | --- | --- |
| No. 1 | 4 weeks | 100 | 100 |
| | 8 weeks | 100 | 100 |
| No. 2 | 4 weeks | 100 | 100 |
| | 8 weeks | 100 | 100 |
| No. 3 | 4 weeks | 100 | 100 |
| | 8 weeks | 100 | 100 |

EXAMPLE 3

(Leaching experiment in accordance with DIN 52,172, p. 1)

The samples obtained as in Example 2 (measuring 5×2.5×1.5cm) are stored in water for 4 periods of 5 days each, interrupted by 2 days' storage in the open after each period in water.

Before being placed in the water, the blocks are subjected to a vacuum to open the pores of the wood. The water used for testing the resistance to leaching is changed twice daily.

The biological action was determined with the aid of termites in the same manner as in Examples 1 and 2.
Results:

| Compound | % Mortality after 4 weeks | after 8 weeks |
| --- | --- | --- |
| No. 1 | 100 | 100 |
| No. 2 | 100 | 100 |
| No. 3 | 80 | 100 |

EXAMPLE 4

90 parts by weight of compound 1 is mixed with 10 parts by weight of N-methyl-α-pyrrolidone. A mixture is obtained which is suitable for application in the form of very fine drops.

EXAMPLE 5

20 parts by weight of compound 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 6

20 parts by weight of compound 3 is dissolved in a mixture consisting of 40 parts of weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 7

20 parts by weight of compound 1 is dissolved in a mixture consisting of 25 parts by weight of cyclohexanol, 65 parts by weight of a mineral oil fraction having a boiling point between 210° and 280° C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 8

20 parts by weight of compound 1 is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 9

40 parts by weight of compound 2 is intimately mixed with 10 parts of the sodium salt of a phenolsulfonic acid-urea-formaldehyde condensate, 2 parts of silica gel and 48 parts of water. A stable aqueous dispersion is obtained. Dilution in 100,000 parts by weight of water gives an aqueous dispersion containing 0.04 wt% of active ingredient.

EXAMPLE 10

20 parts of compound 3 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. A method of inhibiting attack by animal pests in wood or wood-base materials, wherein the wood or wood-base material is contacted with a compound of the formula $$C_nF_{2n+1}-SO_3M,$$

where $n$ denotes one of the integers from 1 to 14 and M denotes hydrogen or a cation.

2. A method as set forth in claim 1 wherein $n$ is an integer of from 3 to 10.

3. A method as set forth in claim 1, wherein $n$ is an integer of 4 to 8.

4. A method as set forth in claim 1, wherein M is hydrogen.

5. A method as set forth in claim 1, wherein M is a cation selected from the group consisting of sodium, potassium, magnesium, calcium, ammonium, $N(CH_3)_3H^+$, $N(C_2H_5)_4^+$, $N(CH_3)_2H_2^+$, and $N(C_4H_9)_4^+$.

6. A method as set forth in claim 1, wherein from about 1 to 10 g of the compound is used per $m^2$ of wood or wood-base surface.

* * * * *